(12) United States Patent
De Lucchi et al.

(10) Patent No.: US 10,913,747 B2
(45) Date of Patent: Feb. 9, 2021

(54) EFFICIENT PROCESS FOR THE PREPARATION OF SITAGLIPTIN THROUGH A VERY EFFECTIVE PREPARATION OF THE INTERMEDIATE 2,4,5-TRIFLUOROPHENYLACETIC ACID

(71) Applicant: F.I.S. - FABBRICA ITALIANA SINTETICI S.P.A., Montecchio Maggiore (IT)

(72) Inventors: Ottorino De Lucchi, Padua (IT); Pierluigi Padovan, Montecchio Maggiore (IT); Elena Brasola, Saccolongo Padova (IT)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 0 days.

(21) Appl. No.: 16/619,299

(22) PCT Filed: May 15, 2018

(86) PCT No.: PCT/EP2018/062508
§ 371 (c)(1),
(2) Date: Dec. 4, 2019

(87) PCT Pub. No.: WO2019/007578
PCT Pub. Date: Jan. 10, 2019

(65) Prior Publication Data
US 2020/0157109 A1    May 21, 2020

(30) Foreign Application Priority Data

Jul. 4, 2017  (EP) .................................... 17179524

(51) Int. Cl.
*C07D 487/04*  (2006.01)
*B01J 27/08*   (2006.01)

(52) U.S. Cl.
CPC ............ *C07D 487/04* (2013.01); *B01J 27/08* (2013.01)

(58) Field of Classification Search
CPC ............................... C07D 487/04; B01J 27/08
USPC ........................................................ 514/250
See application file for complete search history.

(56) References Cited

U.S. PATENT DOCUMENTS

| 5,939,560 A | 8/1999 | Jenkins et al. |
| 2004/0068141 A1 | 4/2004 | Armstrong et al. |
| 2004/0077901 A1 | 4/2004 | Ikemoto et al. |

FOREIGN PATENT DOCUMENTS

| CN | 1749232 A | 3/2006 |
| CN | 101092345 A | 12/2007 |
| CN | 101429115 A | 5/2009 |
| CN | 101823952 A | 9/2010 |
| WO | 9740832 A1 | 11/1997 |
| WO | 9819998 A2 | 5/1998 |
| WO | 2006081151 A1 | 8/2006 |
| WO | 2008078350 A2 | 7/2008 |
| WO | 2009085177 A1 | 7/2009 |

OTHER PUBLICATIONS

Patel, "Biocatalysis: Synthesis of Key Intermediates for Development of Pharmaceuticals", ACS Catalysis, 2011, vol. 1, No. 9, pp. 1056-1074.
Vallejos et al., "A new system for the reduction of 4-hydroxymandelic acids", Bulletin De La Societe Chimique De France, 1997, vol. 134, pp. 101-104.
International Search Report and Written Opinion for Corresponding International Application No. PCT/EP2018/0625508 (10 Pages) (dated Jul. 6, 2018).

*Primary Examiner* — Tracy Vivlemore
*Assistant Examiner* — Ebenezer O Sackey
(74) *Attorney, Agent, or Firm* — Lucas & Mercanti, LLP

(57) ABSTRACT

Object of the present invention is an efficient process for the preparation of the active pharmaceutical ingredient Sitagliptine and the 2,4,5-trifluorophenylacetic acid (TFAA) and salt thereof, which is a key intermediate for the synthesis of Sitagliptine.

20 Claims, No Drawings

EFFICIENT PROCESS FOR THE PREPARATION OF SITAGLIPTIN THROUGH A VERY EFFECTIVE PREPARATION OF THE INTERMEDIATE 2,4,5-TRIFLUOROPHENYLACETIC ACID

CROSS-REFERENCE TO RELATED APPLICATIONS

This application is a 371 of PCT/EP2018/062508, filed May 15, 2018, which claims the benefit of European Patent Application No. 17179524.8, filed Jul. 4, 2017.

TECHNICAL FIELD

The present invention relates to an efficient process for the preparation of the active pharmaceutical ingredient named Sitagliptin, through a very effective process for preparing the intermediate named 2,4,5-trifluorophenylacetic acid.

BACKGROUND ART

The active pharmaceutical ingredient Sitagliptin of formula (I):

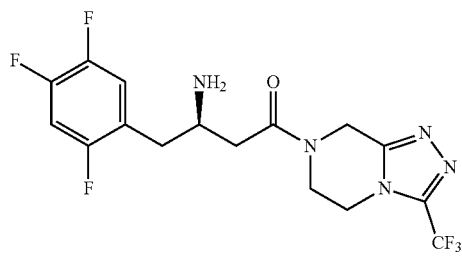

(I)

is a substance also known as MK-0431 and has chemical name 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine and CAS RN 486460-32-6.

This active pharmaceutical ingredient is an oral antihyperglycemic (antidiabetic drug) of the dipeptidyl peptidase-4 (DPP-4) inhibitor. This enzyme-inhibiting drug is used alone or in combination with other oral antihyperglycemic agents, such as for example metformin or a thiazolidinedione, for treatment of diabetes mellitus type 2. The benefit of this medicine is its fewer side effects (e.g. less hypoglycemia, less weight gain) in the control of blood glucose values.

The inhibitors of the dipeptidyl peptidase-4 enzyme are medicines useful in treating diabetes, in particular type 2 diabetes (see for example WO97/40832; WO98/19998; U.S. Pat. No. 5,939,560; Bioorg. Med. Chem. Lett., 6, 1163-1166 (1996); Bioorg. Med. Chem. Lett., 6, 2745-2748 (1996)).

Sitagliptin is a successful active pharmaceutical ingredient with a very high economical turnover.

Sitagliptin is commercially available as the phosphate salt monohydrate, which has CAS RN 654671-77-9, and it is sold as pharmaceutical product under the trade name Januvia®.

Considering the commercial interest for Sitagliptin, many methods for the preparation of said compound have been developed, many of them being addressed to minimize the production costs of said compound.

In particular, according to the knowledge of the Applicant, at the moment have been described about 60 different route of synthesis directed to Sitagliptin and intermediates thereof, part of them described in about 300 patent families directed to them.

Within said very large number synthetic approaches for the preparation of Sitagliptin, each one comprising many steps and many different intermediates, the Applicant's attention has been focused on the methods which involve the intermediate compound named 2,4,5-trifluorophenylacetic acid (abbreviated TFPAA) having the following chemical formula (II):

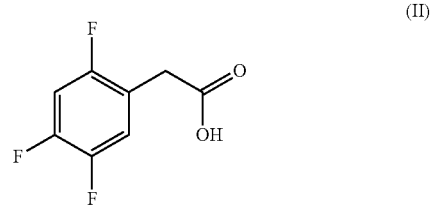 [SMILES: O=C(O)Cc1cc(F)c(F)cc1F]

(II)

and having chemical name 2,4,5-trifluorobenzeneacetic acid.

In literature have been described many method for preparing TFPAA.

In the following pages the most interesting of them have been briefly described.

In particular, US2004/0068141A1 describes a process for the preparation of fluorophenylacetic acids starting from aromatic halides according to the method described in scheme 1 wherein X represents chlorine, bromine or iodine:

Scheme 1.

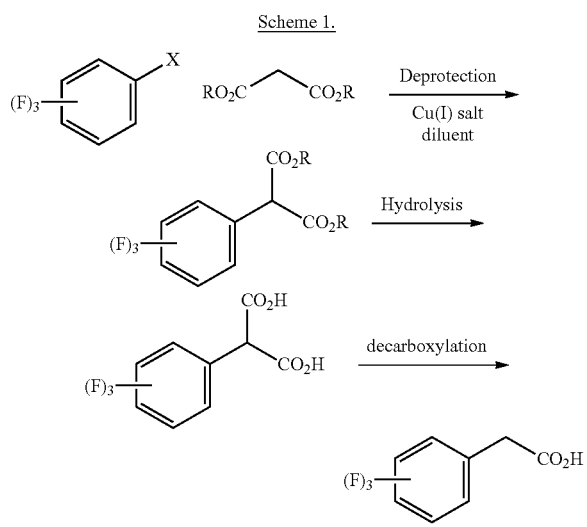

The first step however requires the use of large quantities of copper salts, with related problems of extraction and disposal of the toxic heavy metal, and the aromatic halide used often has high costs.

U.S. application number US2004/077901 describes a process for the preparation TFPAA starting from 1,2,4,5-halo benzene according to the method described in scheme 2:

Scheme 2.

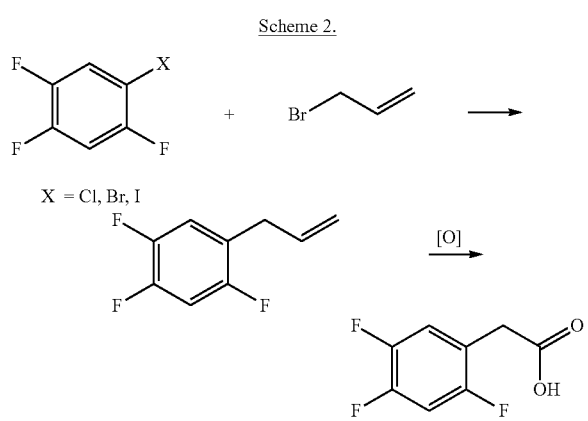

The 1,2,4,5-halo benzene reacts with allyl bromide, and subsequently it is oxidized to give TFPAA.

That synthetic route however requires the use of expensive starting materials, and the relatively harsh reaction conditions which make this method not suitable for industrial production.

Chinese patent CN1749232 describes a three-steps process for the preparation TFPAA starting from 1,2,4-trifluorobenzene according to the following scheme 3:

Scheme 3

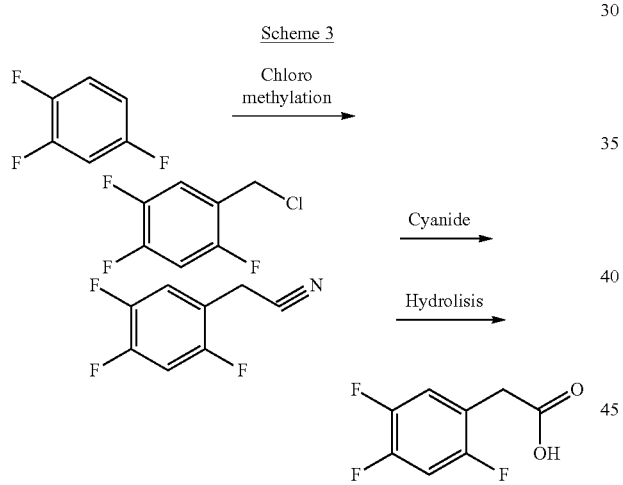

However, the synthesis requires the use of cyanides which is a very toxic reagent.

Chinese patent CN101092345 describes a two-steps process for the preparation of TFPAA starting from 1,2,4-fluorobenzene, according to the following scheme 4:

Schema 4.

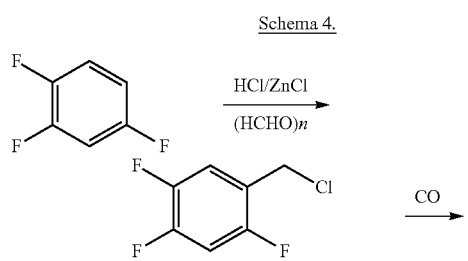

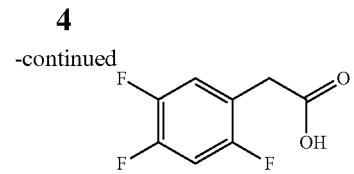

However, the carbonylation reaction is difficult and requires the use of monoxide of carbon which is a toxic gas.

Chinese patents CN101823952 and CN101429115, describes a process for the preparation of TFPAA starting from the intermediate 2,4,5-trifluorobenzyl chloride or bromide, according to the following scheme 5:

Schema 5.

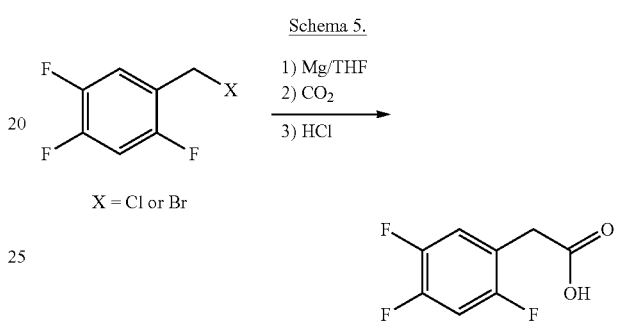

Within many synthetic approaches for the preparation of TFPAA, each one comprising many steps and many intermediates, the Applicant, willing to improve the synthesis of Sitagliptin, has directed his attention to a different route of synthesis of TFPAA, in particular, the one based on the compound 2,4,5-trifluoromandelic acid of formula (III):

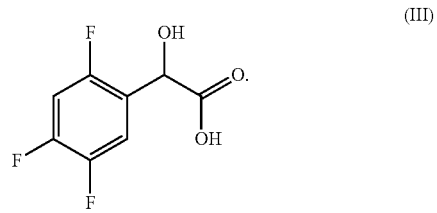 [SMILES: O=C(O)C(O)c1cc(F)c(F)cc1F]

Thus, a dedicated prior art search has retrieved the following two documents dealing with the synthesis of TFPAA through the key intermediate 2,4,5-trifluoromandelic acid.

In particular, the application WO2008/078350 describes a process for the preparation of fluorophenylacetic acids and their derivatives, also comprising 2,4,5-trifluorophenylacetic acid, through 6 steps of synthesis starting from trifluorobenzene, according to the following Scheme 6:

Scheme 6.

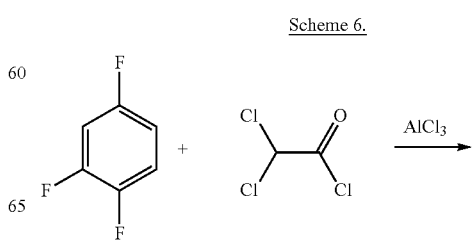

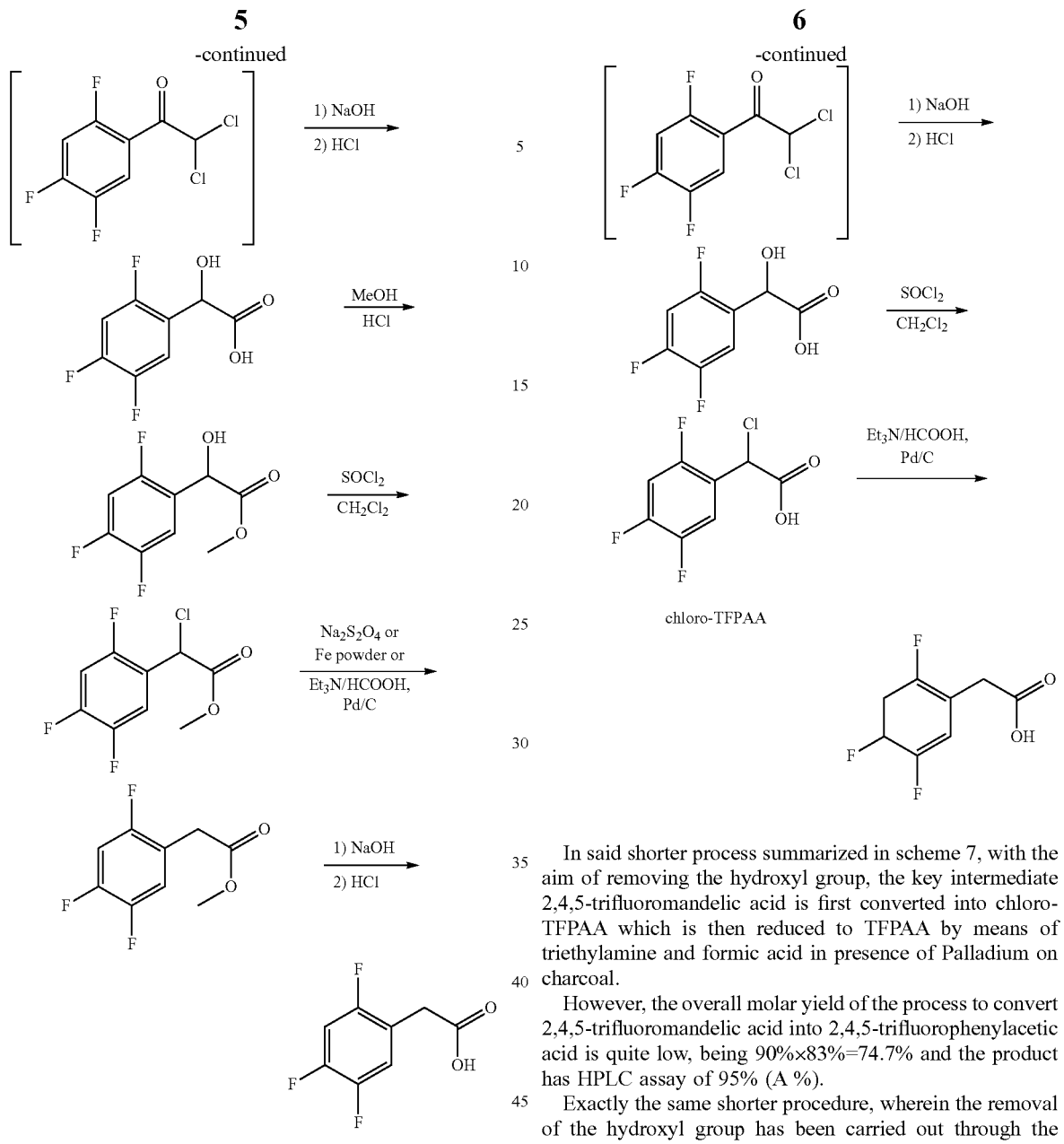

Nevertheless, the route of synthesis above appears to be too long to find ever an actual industrial application for the preparation of TFPAA.

The application WO2008/078350 also describes, in example 4 combined with example 9, a shorter route of synthesis of TFPAA based on 4 steps and summarized in the following reaction scheme 7:

In said shorter process summarized in scheme 7, with the aim of removing the hydroxyl group, the key intermediate 2,4,5-trifluoromandelic acid is first converted into chloro-TFPAA which is then reduced to TFPAA by means of triethylamine and formic acid in presence of Palladium on charcoal.

However, the overall molar yield of the process to convert 2,4,5-trifluoromandelic acid into 2,4,5-trifluorophenylacetic acid is quite low, being 90%×83%=74.7% and the product has HPLC assay of 95% (A %).

Exactly the same shorter procedure, wherein the removal of the hydroxyl group has been carried out through the intermediate chloro-TFPAA, has been studied and described some year later by LIU Ze-ling in Hebei Journal of Industrial Science and Technology, Vol. 28, No. 4, July 2011, pag. 244-246. LIU studied the parameters affecting the reduction reaction of chloro-TFPAA to TFPAA but it appears that the molar yield remained low, i.e. 56.0% as described in the only one example and 65.5% as described in the screening of the amount of Palladium on charcoal.

The prior art methods for the synthesis of TFPAA thus suffer of the drawbacks that the numbers of step is generally high, by the use of hazardous reagents or because they require dedicated special industrial apparatus or, finally, because the overall molar yield is relatively low.

SUMMARY OF INVENTION

The problem addressed by the present invention, in the light of the prior art methods, is therefore that of providing a much more efficient process for the preparation of Sitagliptin, which also avoids the use of toxic reagents.

Another linked problem is provide an cost-effective process for the preparation of Sitaglitpin.

These problems are solved by a process for the preparation of Sitagliptin and salts thereof as outlined in the annexed claims, whose definitions are integral part of the present description.

Particularly, the present invention provides an efficient and cost-effective process for the preparation of Sitagliptin.

Further features and advantages of the process according to the invention will result from the description hereafter reported of examples of realization of the invention, provided as an indication of the invention.

DESCRIPTION OF EMBODIMENTS

The object of the present invention is a process for the preparation of Sitagliptin of formula (I) or salt thereof:

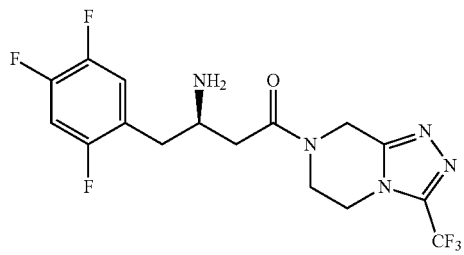

comprising of the following steps:
A) preparation of 2,4,5-trifluorophenylacetic acid of formula (II) or salt thereof:

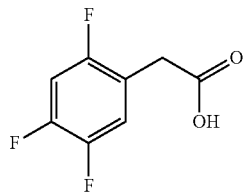

by direct conversion of the compound of (III):

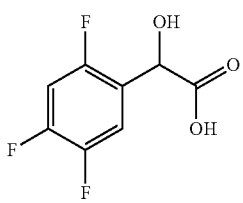

to the compound of formula (II),
wherein said direct conversion is carried out by reduction reaction;
B) conversion of 2,4,5-trifluorophenylacetic acid of formula (II) obtained in the step A) to obtain Sitagliptin.

Differently from the prior art processes, it has indeed surprisingly found that it is possible to carry out the direct conversion of 2,4,5-trifluoromandelic acid of formula (III) to 2,4,5-trifluorophenylacetic acid of formula (II) (abbreviated TFPAA).

The direct conversion of 2,4,5-trifluoromandelic acid to TFPAA is carried out by means of a reduction reaction.

Although, it would be expected that in the reaction conditions wherein the hydroxyl group is cleaved also the aromatic ring would be hydrodefluorinated, the process of the invention instead provides as product TFPAA, i.e. the potentially competing hydrodefluorination reaction does not occur.

According to the invention, the process for the preparation of Sitagliptin of formula (I) and salt thereof, comprises also the step B) which is carried out by means of the following steps:
C) the conversion of 2,4,5-trifluorophenylacetic acid of formula (II) obtained in the step A) to Ketoamide of formula (IV):

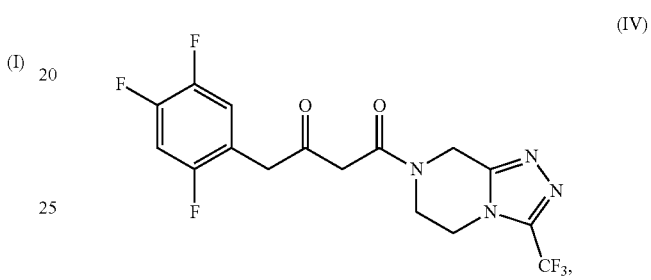

D) the amination reaction of Ketoamide of formula (IV) produced in the step C) to give Enamine Amide of formula (V):

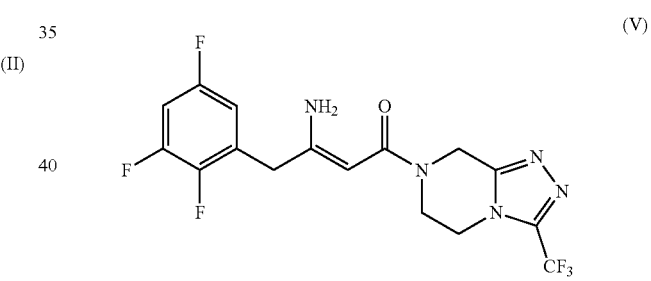

E) the conversion of Enamine Amide of formula (V) obtained in the step D) to Sitagliptin of formula (I):

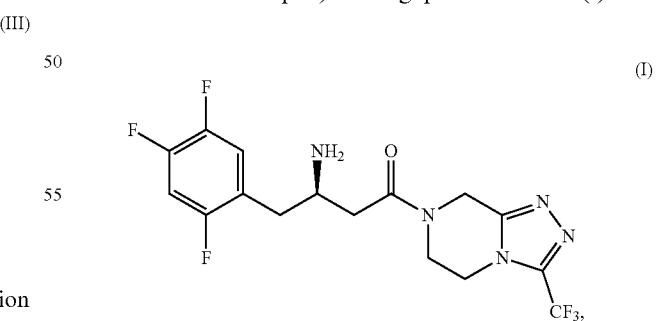

or by means the alternative process for obtaining Sitagliptin, wherein the steps D) and E) are substituted by the following step:
D1) the enzymatic conversion of Ketoamide of formula (IV), obtained by previous step C), to Sitagliptin of formula (I):

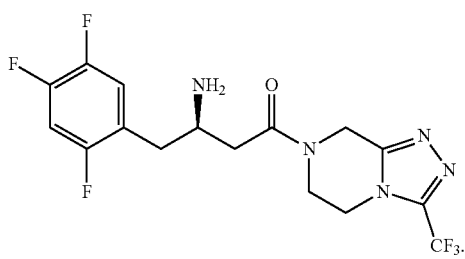

(I)

In particular, the Ketoamide compound of formula (IV) of the step C) is produced starting from TFPAA according to the known prior art methods, such as, for instance, those disclosed in WO2005/020920, purposely in the Step A of example 1 at pag. 12 and 13, which refers to scheme 2 of the example 1 at pag. 11 and 12.

In particular the step C) can be carried out firstly by reaction of TFPAA with Meldrum's acid, in presence of 4-(dimethylamino)pyridine, N,N-diisopropylethylamine and pivaloyl chloride. The intermediate compound thus prepared of formula:

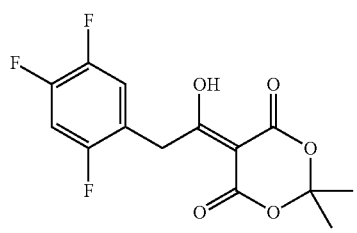 [SMILES: CC1(C)OC(=O)C(=C(O)Cc2cc(F)c(F)cc2F)C(=O)O1]

is then reacted with Triazole compound, as hydrochloride salt, of formula:

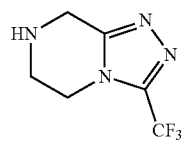

to provide the Ketoamide of formula (IV).

In the following step of the process, i.e. in the step D), the Ketoamide of formula (IV) produced in the step C) is converted into Enamine Amide of formula (V). Said conversion can be carried out, for instance, according the teaching of WO2007/050485, in particular the Step B at pag. 35 which refers to scheme 2 at pag. 34. In particular, in the step D), the Ketoamide of formula (IV) is reacted with ammonium acetate and ammonium hydroxide to provide the Enamina Amide of formula (V).

The step of conversion of Enamine Amide of formula (V) produced in the step D) to Sitagliptin of formula (I) can be carried out, for instance, according to the teaching of WO2007/050485, in particular the Step C at pag. 35 which refers to scheme 2 at pag. 34. In particular, the Enamina Amide of formula (V) is converted to Sitagliptin of formula (I) by asymmetric hydrogenation catalized by a Rodium catalyst, more particularly a catalyst comprising Rodium and Josiphos as ligand.

The alternative process for obtaining Sitagliptin by the step D1), starting from Ketoamide of formula (IV) beforehand described, consists in the enzymatic conversion of said Ketoamide obtained in the step C) to Sitagliptin of formula (I). This enzymatic conversion is described by C. K. Savile at al., in the article Science, 2010, volume 329, pag. 305-309. In particular, the Ketoamide compound of formula (IV) can be converted to Sitagliptin by means of a transaminase enzyme in presence of isoproprylamine. Savile at al., also disclose improved conditions to perform the conversion of the step D1).

The process of the present invention, can also comprise the following previous steps for the preparation of the compound of formula (III):

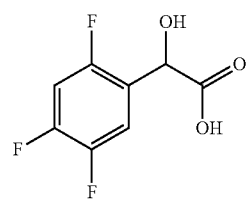

(III)

said previous steps being the following steps:
a) acylation of the 1,3,4-trifluorobenzene of formula (VI):

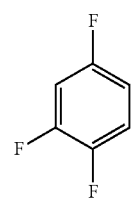

(VI)

with dichloroacetylchloride to give the compound of formula (VII):

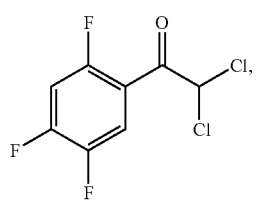

(VII)

b) conversion of the compound of formula (VII) prepared in the step a) to the compound of formula (III):

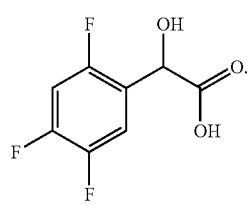

(III)

Thus, considering the steps a) and b), starting from 1,3,4-trifluorobenzene, the process for the preparation of TFPAA of formula (II) consists in only three steps.

The process for obtaining the compound of formula (III) beforehand described, starting from 1,3,4-trifluorobenzene of formula (VI), consists in the step a) in the acylation of said compound (VI), to obtain the compound of formula (VII). Then, following the process, in the step b), the conversion of the compound of formula (VII) to the compound of formula (III) which can be carried out by treatment under basic condition, in particular with sodium hydroxide.

According to a preferred embodiment, the steps a) and b) can be carried out consequentially, without to isolate the compound of formula (VII).

The step a) of acylation of 1,3,4-trifluorobenzene with dichloroacetylchloride can be carried out in presence of a Lewis acid, such as, for instance AlCl₃.

The step b), i.e. the conversion of the compound of formula (VII) to the compound of formula (III) can be carried out by treatment with a base in an organic solvent. According to a preferred embodiment, the step b) is carried out by means of aqueous sodium hydroxide in dichloromethane, as solvent.

The molar yield of the step a) and b) combined and carried out consequentially, i.e. without to isolate the compound of formula (VII) is typically about 84% to about 90%. The product 2,4,5-trifluoromandelic acid of formula (III) has 98-99% chemical purity by HPLC A/A %.

Optionally, the 2,4,5-trifluoromandelic acid of formula (III) obtained in the step b) can be purified by recrystallization form water. The yield of said crystallization is about 86%. The purified 2,4,5-trifluoromandelic acid of formula (III) has then chemical purity from 99.2% to 99.7% by HPLC A/A % with maximum impurity 0.2% by HPLC A/A %.

Thus, according to a preferred embodiment, the process allows the preparation of TFPAA of formula (II), starting from 1,3,4-trifluorobenzene of formula (VI) in only two physical steps, i.e. performing only the isolation of the compound of formula (III), according to the following scheme 8:

Scheme 8.

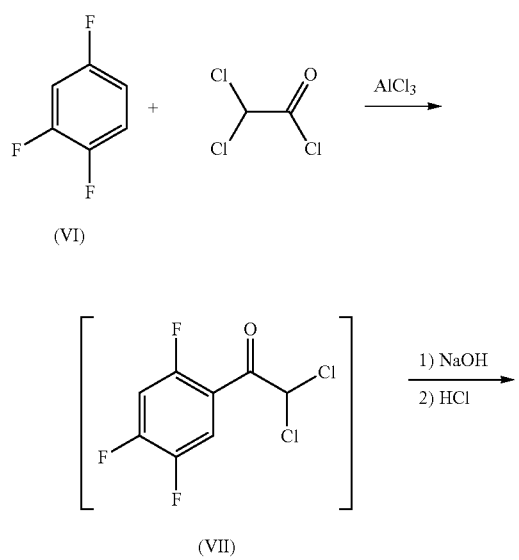

(VI)

(VII)

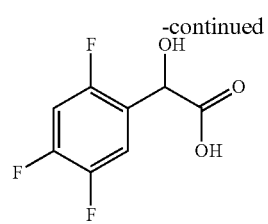

(III)

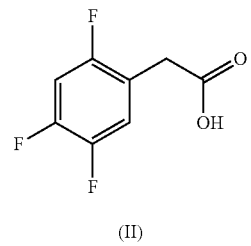

(II)

In the step A) of the present invention, the compound 2,4,5-trifluoromandelic acid of formula (III):

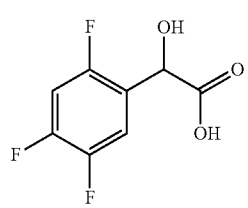

(III)

is directly converted into 2,4,5-trifluorophenylacetic acid of formula (II) or salt thereof:

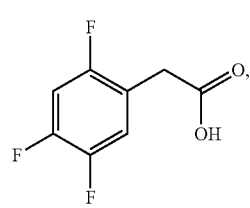

(II)

i.e. without the formation of other intermediates.

The step A) of direct conversion of the compound of formula (III) to the compound of formula (II) is carried out by a reduction reaction.

The stoichiometry of said reduction reaction foresees the addition of hydrogen atoms and the formation, as by-product, of water.

The reduction reaction of the step A) is carried out in presence of iodide catalyst.

The iodide catalyst that can be used to carry out the step A) of process of the present invention can be selected in the group comprising of iodine, sodium iodide, potassium iodide, hydroiodic acid, lithium iodide, ammonium iodide.

According to a more preferred embodiment, the iodide catalyst is iodine or sodium iodide.

The reduction reaction of the step A) is carried out in presence of a phosphorus and/or sulphurous reductant.

The phosphorus and/or sulphurous reductant that can be used to carry out the step A) of the process of the present invention can be selected in the group comprising of phosphorous acid, hypophosphorous acid, pyrophosphoric acid, triphosphoric acid, trimethaphosphoric acid, hypophosphoric acid, red phosphorus, sulfurous acid, pyrosulfurous acid, peroxymonosulfuric acid, hyposulfurous acid.

According to the preferred embodiment, the phosphorus and/or sulphurous reductant is phosphorous acid.

The step A) of process of the present invention can be carried out in an acid solvent or an aqueous acid mixture thereof.

The acid solvent or an aqueous acid mixture thereof to carry out step A) can be chosen in the group comprising of hydroiodic acid, hydrobromic acid, acetic acid, methansulphonic acid, trifluoromethansulphonic acid.

According to preferred embodiment, the acid solvent or an aqueous acid mixture thereof can be chosen in the group comprising of hydrobromic acid, acetic and methansulphonic acid.

According to a more preferred embodiment, the acid solvent or an aqueous acid mixture thereof is methansulphonic acid since it is the acid that provide the higher reaction rate, i.e. allow the end of the reduction reaction in the shortest time.

According to the preferred embodiment, the acid solvent or an aqueous acid mixture thereof can be an aqueous acid mixture thereof. Examples of an aqueous acid mixture can be a mixture of acetic acid and water or a mixture of methansulphonic acid and water, for instance, a mixture 3:2 (v/v) of methansulphonic acid and water.

According to the a more preferred embodiment, the acid solvent or an aqueous acid mixture thereof is methansulphonic acid or is a mixture of methansulphonic acid and water.

According to the an again more preferred embodiment, the acid solvent or an aqueous acid mixture thereof is methansulphonic acid.

The reduction reaction of step A) is carried out by a phosphorus and/or sulphurous reductant.

The reduction reaction of step A) is carried out in presence of a iodide catalyst and in an acid solvent or an aqueous acid mixture thereof.

According to an embodiment, the reduction reaction of step A) is carried out by a phosphorus and/or sulphurous reductant, in presence of a iodide catalyst.

According to an embodiment, the reduction reaction of step A) is carried out by a phosphorus and/or sulphurous reductant, in presence of a iodide catalyst and in an acid solvent or an aqueous acid mixture thereof.

According to a preferred embodiment, the reduction reaction of step A) is carried out by a phosphorus and/or sulphurous reductant, in presence of a iodide catalyst and in an acid solvent or an aqueous acid mixture thereof which is chosen in the group comprising of hydroiodic acid, hydrobromic acid, acetic acid, methansulphonic acid, trifluoromethansulphonic acid.

According to a more preferred embodiment, the reduction reaction of step A) is carried out by a phosphorus and/or sulphurous reductant, in presence of a iodide catalyst and in an acid solvent or an aqueous acid mixture thereof which is chosen in the group comprising of hydrobromic acid, acetic acid and methansulphonic acid.

According to a preferred embodiment, the reduction reaction of step A) is carried out by a phosphorus and/or sulphurous reductant, in presence of a iodide catalyst and in an acid solvent or an aqueous acid mixture thereof chosen in the group comprising of hydrobromic acid, acetic acid, and methansulphonic acid.

According to a more preferred embodiment, the reduction reaction of step A) is carried out by under the following conditions: the iodine catalyst is iodine or sodium iodide, the phosphorus and/or sulphurous reductant is phosphorous acid, and the acid solvent or an aqueous acid mixture thereof is selected in the group comprising of hydrobromic acid, acetic acid, methansulphonic acid, being more preferred methansulphonic acid.

According to an more preferred embodiment, the reduction reaction of step A) is carried out by phosphorous acid as phosphorus and/or sulphurous reductant, in presence of a iodide catalyst and in an acid solvent or an aqueous acid mixture thereof chosen in the group comprising of hydrobromic acid, acetic acid, and methansulphonic acid.

According to another preferred embodiment, the reduction reaction of step A) is carried out by a phosphorus and/or sulphurous reductant, in presence of a iodine or sodium iodide as iodide catalyst and in an acid solvent or an acid mixture thereof chosen in the group comprising of hydrobromic acid, acetic acid, and methansulphonic acid.

According to another preferred embodiment, the reduction reaction of step A) is carried out by phosphorous acid as a phosphorus and/or sulphurous reductant, in presence of a iodine or sodium iodide as iodide catalyst.

According to an again more preferred embodiment, the reduction reaction of step A) is carried out by phosphorous acid as a phosphorus and/or sulphurous reductant, in presence of iodine or sodium iodide as iodide catalyst and in an acid solvent or an aqueous acid mixture thereof chosen in the group comprising of hydrobromic acid, acetic acid, and methansulphonic acid.

According to an again more preferred embodiment, the reduction reaction of step A) is carried out by phosphorous acid as a phosphorus and/or sulphurous reductant, in presence of iodine or sodium iodide as iodide catalyst and in an acid solvent or an aqueous acid mixture thereof being methansulphonic acid.

The amount of Iodide catalyst that can be used to carry out the step A) ranges between 0.05 and 0.5 molar equivalents compared to the starting compound of formula (III).

According to a preferred embodiment, to carry out the step A) from 0.1 to 0.3 molar equivalents of Iodide catalyst are used.

According to a preferred embodiment, to carry out the step A) from 0.1 to 0.2 molar equivalents of Iodide catalyst are used.

According to a more preferred embodiment, to carry out the step A) 0.1 molar equivalents of iodine or sodium iodide as Iodide catalyst are used.

According to a more preferred embodiment, to carry out the step A) 0.1 molar equivalents of iodine as Iodide catalyst are used.

The amount of phosphorus and/or sulphurous reductant that can be used to carry out the step A) ranges between 1.5 and 8 molar equivalents compared to the starting compound of formula (III).

According to a preferred embodiment, to carry out the step A) from 3 to 6 molar equivalents of phosphorus and/or sulphurous reductant are used.

According to a more preferred embodiment, to carry out the step A) 3 molar equivalents of phosphorous acid as phosphorus and/or sulphurous reductant are used.

According to a more preferred embodiment, to carry out the step A) 4 molar equivalents of phosphorous acid as phosphorus and/or sulphurous reductant are used.

According to an embodiment of the invention, the step A) can be carried out using 0.3 molar equivalents of sodium iodide as Iodide catalyst and 3 molar equivalents of phosphorous acid as phosphorus and/or sulphurous reductant.

According to an embodiment of the invention, the step A) can be carried out using 0.3 molar equivalents of sodium iodide as Iodide catalyst and 3 molar equivalents of phosphorous acid as phosphorus and/or sulphurous reductant and using an acid solvent or an aqueous acid mixture thereof.

According to a preferred embodiment of the invention, the step A) can be carried out using 0.3 molar equivalents of sodium iodide as Iodide catalyst and 3 molar equivalents of phosphorous acid as phosphorus and/or sulphurous reductant and using methansulphonic acid as an acid solvent or an aqueous acid mixture thereof.

According to a more preferred embodiment of the invention, the step A) can be carried out using 0.3 molar equivalents of sodium iodide as Iodide catalyst and 3 molar equivalents of phosphorous acid as phosphorus and/or sulphurous reductant and using, as an acid solvent or an aqueous acid mixture thereof, a mixture 3:2 of methansulphonic acid and water.

According to an embodiment of the invention, the step A) can be carried out using 0.1 molar equivalents of iodine or sodium iodide as Iodide catalyst and 4 molar equivalents of phosphorous acid as phosphorus and/or sulphurous reductant.

According to an embodiment of the invention, the step A) can be carried out using 0.1 molar equivalents of iodine or sodium iodide as Iodide catalyst and 4 molar equivalents of phosphorous acid as phosphorus and/or sulphurous reductant and using an acid solvent or an aqueous acid mixture thereof.

According to a preferred embodiment of the invention, the step A) can be carried out using 0.1 molar equivalents of iodine or sodium iodide as Iodide catalyst and 4 molar equivalents of phosphorous acid as phosphorus and/or sulphurous reductant and using methansulphonic acid as an acid solvent or an aqueous acid mixture thereof.

According to a more preferred embodiment of the invention, the step A) can be carried out using 0.1 molar equivalents of iodine or sodium iodide as Iodide catalyst and 4 molar equivalents of phosphorous acid as phosphorus and/or sulphurous reductant and using, as an acid solvent or an aqueous acid mixture thereof, a mixture 3:2 of methansulphonic acid and water.

The step A) is concluded in less than 45 hours, typically in 15-30 hours.

The step A) is concluded in less than 45 hours, typically in 10-15 hours.

The step A) provides the product TFPAA of formula (II) with chemical purity of the not-isolated crude product of 93-97%, as determined by HPLC A/A %.

The step A) provides the product TFPAA of formula (II) with chemical purity of the isolated crude product of 93-97%, typically about 95%, as determined by HPLC A/A % and molar yield of 87-90%.

It should be noted as said molar yield of 87-90% of the direct conversion of the compound of formula (III) to the compound of formula (II) is remarkably higher than the molar yield described in prior art for preparing (II) starting from (III) via intermediates, which is at best 74.7% (achieving the same level of chemical purity), as discusses in the background art section The chemical purity of the product TFPAA can be further increased by recrystallization of the product, for example by heating and then cooling the product within 4 volumes of toluene, thus achieving TFPAA with a chemical purity higher than 99.7%, typically about 99.8%, as determined by HPLC A/A %, and overall molar yield, stating from the compound of formula (III) of about 80%.

According to another embodiment of the invention, the step A) can be carried out using from 0.1 to 0.3 molar equivalents of iodine or sodium iodide as Iodide catalyst and from 3 to 6 molar equivalents of phosphorous acid as phosphorus and/or sulphurous reductant and using, as an acid solvent or an aqueous acid mixture thereof, methansulphonic acid.

According to a more preferred embodiment of the invention, the step A) can be carried out using from 0.1 to 0.3 molar equivalents of sodium iodide as Iodide catalyst and from 3 to 6 molar equivalents of phosphorous acid as phosphorus and/or sulphurous reductant and using, as an acid solvent or an aqueous acid mixture thereof, from 1 to 3 volumes of methansulphonic acid. This combination of conditions provides indeed highest molar yield and highest chemical purity of the product TFPAA (see example 3).

According to an again more preferred embodiment of the invention, the step A) can be carried out using 0.1 molar equivalents of sodium iodide as Iodide catalyst and 6 molar equivalents of phosphorous acid as phosphorus and/or sulphurous reductant and using, as an acid solvent or an aqueous acid mixture thereof, 2 volumes of methansulphonic acid. This combination of conditions provides indeed best molar yield and best chemical purity of the product TFPAA (see example 3).

According to another embodiment of the invention, the step A) can be carried out using 0.1 molar equivalents of sodium iodide as Iodide catalyst and 6 molar equivalents of phosphorous acid as phosphorus and/or sulphurous reductant and using, as an acid solvent or an aqueous acid mixture thereof, 0.5 molar equivalents of methansulphonic acid (see example 4).

According to a preferred embodiment, whichever is the catalyst or the reductant, the step A) is carried out in absence of water, since it provides higher molar yield of the product of formula (II), compared with conditions wherein water is present.

According to a more preferred embodiment, the step A) is carried out in absence of water and is carried out by phosphorous acid as a phosphorus and/or sulphurous reductant, in presence of a iodine or sodium iodide as iodide catalyst and in an acid solvent chosen in the group comprising of hydrobromic acid, acetic acid, and methansulphonic acid, being more preferred methansulphonic acid.

According to an again more preferred embodiment of the invention, the step A) is carried out in absence of water and can be carried out using from 0.1 to 0.3 molar equivalents of sodium iodide as Iodide catalyst and from 3 to 6 molar equivalents of phosphorous acid as phosphorus and/or sulphurous reductant and using, as an acid solvent, from 1 to 3 volumes of methansulphonic acid. This combination of conditions provides indeed highest molar yield and highest chemical purity of the product TFPAA (see example 3).

The amount of the acid solvent or an aqueous acid mixture thereof that can be used to carry out the step A) ranges between 0.05 and 2 molar equivalents compared to the starting compound of formula (III).

According to a preferred embodiment, to carry out the step A) from 0.05 to 0.5 molar equivalents of the acid solvent or an aqueous acid mixture thereof.

According to a more preferred embodiment, to carry out the step A) 0.1 molar equivalents of the acid solvent or an aqueous acid mixture thereof.

The reduction reaction of step A) is carried out in presence of a iodide catalyst and in an acid solvent or an aqueous acid mixture thereof.

According to a more preferred embodiment, the reduction reaction of step A) is carried out by under the following conditions: the iodine catalyst is iodine, the phosphorus and/or sulphurous reductant is phosphorous acid, and the acid solvent or an aqueous acid mixture thereof is selected in the group comprising of hydrobromic acid, acetic acid, methansulphonic acid, being more preferred methansulphonic acid.

According to an more preferred embodiment, the reduction reaction of step A) is carried out by phosphorous acid as phosphorus and/or sulphurous reductant, in presence of a iodide catalyst and in an acid solvent or an aqueous acid mixture thereof chosen in the group comprising of hydrobromic acid, acetic acid, and methansulphonic acid.

According to another preferred embodiment, the reduction reaction of step A) is carried out by a phosphorus and/or sulphurous reductant, in presence of a iodine as iodide catalyst and in an acid solvent or an aqueous acid mixture thereof chosen in the group comprising of hydrobromic acid, acetic acid, and methansulphonic acid.

According to another preferred embodiment, the reduction reaction of step A) is carried out by phosphorous acid as a phosphorus and/or sulphurous reductant, in presence of a iodine as iodide catalyst.

According to an again more preferred embodiment, the reduction reaction of step A) is carried out by phosphorous acid as a phosphorus and/or sulphurous reductant, in presence of a iodine as iodide catalyst and in an acid solvent or an aqueous acid mixture thereof chosen in the group comprising of hydrobromic acid, acetic acid, and methansulphonic acid.

According to an again more preferred embodiment, the reduction reaction of step A) is carried out by phosphorous acid as a phosphorus and/or sulphurous reductant, in presence of a iodine as iodide catalyst and in an acid solvent or an aqueous acid mixture thereof being methansulphonic acid.

According to an embodiment of the invention, the step A) can be carried out using 0.1 molar equivalents of iodine as Iodide catalyst and 4 molar equivalents of phosphorous acid as phosphorus and/or sulphurous reductant.

According to an embodiment of the invention, the step A) can be carried out using 0.1 molar equivalents of iodine as Iodide catalyst and 4 molar equivalents of phosphorous acid as phosphorus and/or sulphurous reductant and using an acid solvent or an aqueous acid mixture thereof.

According to a preferred embodiment of the invention, the step A) can be carried out using 0.1 molar equivalents of iodine as Iodide catalyst and 4 molar equivalents of phosphorous acid as phosphorus and/or sulphurous reductant and using methansulphonic acid as an acid solvent or an aqueous acid mixture thereof.

In preferred embodiments, step A) is conducted at a temperature between 90° C. and 120° C. More preferably, the temperature in step A) is comprised between 90° C. and 110° C. More preferably, the temperature in step A) is comprised between 95° C. and 105° C.

According to a more preferred embodiment, the step A) can be carried out using the iodide catalyst is in the amount between 0.05 and 0.5 molar equivalents compared to the compound of formula (III), the phosphorus and/or sulphurous reductant is in the amount between 1.5 and 8 molar equivalents compared to the compound of formula (III), and the acid solvent or an aqueous acid mixture thereof in the amount between 0.05 and 2 molar equivalents compared to the compound of formula (III).

According to another embodiment of the invention, the step A) can be carried out using from 0.05 to 0.2 molar equivalents of iodine as Iodide catalyst and from 3 to 6 molar equivalents of phosphorous acid as phosphorus and/or sulphurous reductant and using, as an acid solvent or an aqueous acid mixture thereof, methansulphonic acid.

According to a more preferred embodiment of the invention, the step A) can be carried out using from 0.05 to 0.2 molar equivalents of iodine as Iodide catalyst and from 3 to 6 molar equivalents of phosphorous acid as phosphorus and/or sulphurous reductant and using, as an acid solvent or an aqueous acid mixture thereof, from 0.05 to 0.3 equivalet of methansulphonic acid. This combination of conditions provides indeed highest molar yield and highest chemical purity of the product TFPAA.

According to an again more preferred embodiment of the invention, the step A) can be carried out using 0.1 molar equivalents of iodine as Iodide catalyst and 4 molar equivalents of phosphorous acid as phosphorus and/or sulphurous reductant and using, as an acid solvent or an aqueous acid mixture thereof, 0.1 equivalent of methansulphonic acid. This combination of conditions provides indeed best molar yield and best chemical purity of the product TFPAA.

According to another embodiment of the invention, the step A) can be carried out using 0.1 molar equivalents of iodine as Iodide catalyst and 4 molar equivalents of phosphorous acid as phosphorus and/or sulphurous reductant and using, as an acid solvent or an aqueous acid mixture thereof, 0.1 molar equivalents of methansulphonic acid.

The compound 2,4,5-trifluorophenylacetic acid of formula (II) or salt thereof:

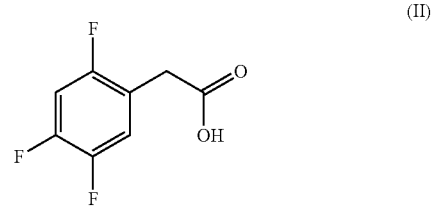 [SMILES: O=C(O)Cc1cc(F)c(F)cc1F]

(II)

can be thus prepared by direct conversion of the compound of (III):

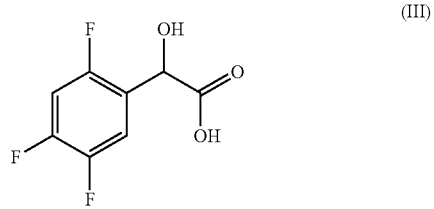 [SMILES: O=C(O)C(O)c1cc(F)c(F)cc1F]

(III)

to the compound of formula (II),
wherein said direct conversion is carried out by reduction reaction.

Moreover, the condition discussed above to carry out the step A) also apply to said preparation of TFPAA of formula (II) starting from the compound of formula (III).

In particular, said reduction reaction (of step A)) is carried out in presence of iodide catalyst and with a phosphorus and/or sulphurous reductant and is carried out in an acid solvent or an aqueous acid mixture thereof.

More particularly, the reduction reaction of step A) is carried out in presence of iodine or sodium iodide, with phosphorous acid and methansulphonic acid.

A phosphorus and/or sulphurous reductant, particularly phosphorous acid, or iodine, or a iodide salt, particularly sodium iodide, or methansulphonic acid can be thus used to carry out the conversion of the compound of formula (III):

(III)

to 2,4,5-trifluorophenylacetic acid of formula (II) or salt thereof:

(II)

In one embodiment of the present invention, Sitagliptin of formula (I) or salt thereof, prepared according to the above process, may be included in pharmaceutical compositions, comprising one or more pharmaceutically acceptable excipients or in combination with other active pharmaceutical ingredients and one or more pharmaceutically acceptable excipients.

Example of suitable pharmaceutical composition, in particular in combination with other active pharmaceutical ingredients, is a tablet comprising 50 mg of Sitagliptin (as phosphate monohydrate salt) and 850 mg of metformin hydrochloride.

Other examples suitable pharmaceutical compositions are following described:
  25 mg tablet contains sitagliptin phosphate monohydrate, equivalent to 25 mg sitagliptin,
  50 mg tablet contains sitagliptin phosphate monohydrate, equivalent to 50 mg sitagliptin,
  100 mg tablet contains sitagliptin phosphate monohydrate, equivalent to 100 mg sitagliptin,
wherein the above pharmaceutical compositions contain the following excipients in tablet core: microcrystalline cellulose (E460), calcium hydrogen phosphate, anhydrous (E341), croscarmellose sodium (E468), magnesium stearate (E470b) and sodium stearyl fumarate.

Furthermore the film coating of the said pharmaceutical compositions can be made up the following excipients: poly(vinyl alcohol), macrogol 3350, talc (E553b), titanium dioxide (E171), red iron oxide (E172) and yellow iron oxide (E172).

All of the intermediates and compounds of the present invention in particular those of formula (II), (III), (IV), (V), (VII) can be in isolated or in not isolated form, from the reaction mixture wherein they are prepared.

According to the preferred embodiment, all of the intermediates and compounds isolated are typically in form of a solid or of an isolated oil.

According to the preferred embodiment, all of the intermediates and compounds not isolated are typically in form of solution with an organic solvent or water.

The skilled in the art of organic chemistry can appreciate as the process of the invention allows an improvement of the productivity considering the reductions of number of steps employed to carry out the synthesis of Sitagliptin, and, at the same time, avoiding the use of toxic reagents.

EXPERIMENTAL SECTION

The starting material 1,3,4-Trifluorobenzene, dichloroacetyl chloride, are reactants largely commercially available, for example, for supplied by Sigma-Aldrich (USA).

The starting material Triazole having the following formula or the hydrochloride salt:

employed for the synthesis of Ketoamide of formula (IV) in the step C), is reactants largely commercially available, for example, for supplied by Alfa Aesar (Germany), Toronto Research Chemicals Product List, abcr GmbH Product List, Sigma-Aldrich (USA).

A few methods for the preparation of Triazole have been described, for example, Jaume Balsellsin at all in Organic Letters, 7 (6), 1039-1042, 2005 described the synthesis of [1,2,4]Triazolo[4,3-r]piperazines via condensation of high reactive chloromethyloxadiazoles with ethylenediamins.

Alternatively, WO2004/080958 described, in the example 1, in particular Step D, the preparation of 3-(trifluoromethyl)-5,6,7,8-tetrahydro[1,2,4]triazolo[4,3-a]pyrazine, hydrochloride salt (1-4).

Moreover, the synthesis of Triazole is described in the steps from A to D C, related to scheme 1, at pag 32 of WO2007/050485.

Volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance.

Example 1: Preparation of 2,4,5-Trifluoromandelic Acid, Compound (III)

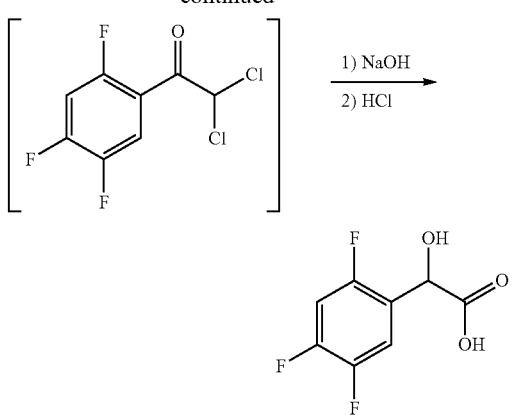

Under inert atmosphere, 200 g aluminium trichloride in 100 g 1,2,4-trifluorobenzene is suspended, the mixture is heated to 60° C., and 167 g dichloroacetyl chloride is added dropwise. Once the conversion is completed (by GC), the mixture is cooled to room temperature and it is taken up again with methylene chloride and water. The layers are separated and the organic layer is concentrated in vacuum. The reaction raw-material is then added dropwise on a mixture of 900 mL water and 90 g sodium hydroxide at 60° C. Once the conversion is completed, the mixture is cooled to room temperature, it is filtered and acidified with concentrated hydrochloric acid to pH=1. The suspension is cooled to 0° C. and it is filtered, isolating 130 g (84%) of product as a white solid with 98% HPLC purity (A %).

$^1$H-NMR (300 MHz, DMSO-$d_6$): δ (ppm) 3.92 (bs, 1H); 4.85 (s, 1H}; 7.4-7.6 (m, 2H); 12.9 (bs, 1H).

Example 2: Preparation of 2,4,5-Trifluoromandelic Acid, Compound (III)

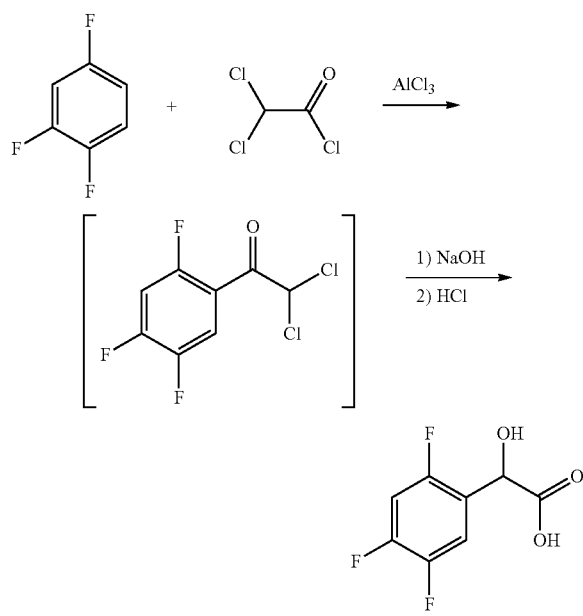

| Material table | | | |
|---|---|---|---|
| Material | Amount | MW | Eq |
| 1,2,4-Trifluorobenzene | 100.0 g | 132.08 | 1 eq |
| AlCl$_3$ | 181.7 g | 133.35 | 1.8 eq |
| dichloroacetyl chloride | 167.4 g | 147.39 | 1.5 eq |
| 30% NaOH | 303 g | 40 | 3 eq |
| H$_2$O | 675 mL | — | 6.75 V |
| CH$_2$Cl$_2$ | 400 mL | — | 4 V |
| 30% HCl | 48.5 mL | — | 6.37 eq |

A 500 mL 4-necks round-bottom flask was charged, under nitrogen atmosphere, with 181.7 g aluminium trichloride (1.8 eq.), 100.0 g of 1,2,4-trifluorobenzene, the mixture is heated to 60° C., and 167.4 g dichloroacetyl chloride ware added dropwise in a period of 1.5 hours.

After the end of addition, the mixture was stirred at 60° C. for further 3 hours. Once the conversion is completed (control by GC; conversion to 2,4,5-trifluorobenzene-dichloroacetophone >99.0%), the mixture was cooled to temperature below 35° C. and then 200 mL of methylene chloride was added. The reaction mixture was added dropwise on 500 mL of H$_2$O, cooled at 0° C., under stirring. The rate of addition was adjusted in order to keep the temperature below 30° C. The mixture was stirred for 15 min, then the layers were separated. A solution of 2,4,5-trifluorobenzene-dichloroacetophone in methylene chloride was obtained with a purity of 96.1% (HPLC A/A %).

A 1 L flask equipped with stirrer, thermometer and condenser, was charged with 675 g of water and 100.0 g sodium hydroxide aq. solution 30%, then, the solution of methylene chloride containing 2,4,5-trifluorobenzene-dichloroacetophone as prepared above was added dropwise to the stirred aqueous layer keeping the temperature below 40° C. After the end of the addition, the mixture was kept under stirring at 40° C. for further 1 hour.

After 30 min. at 40° C. the pH was checked: if pH<8, further NaOH was added up to pH>8. Once the conversion is completed (GC analysis, complete consumption of 2,4,5-trifluorobenzene-dichloroacetophenone), the mixture is cooled to temperature below to 35° C., and the organic solvent was discharged and eliminated. To the obtained aqueous mixture were added 200 mL of CH$_2$Cl$_2$. The mixture was stirred for 15 min, then the layers were separated and the organic solvent was discharged and eliminated. To the obtained aqueous mixture, cooled at room temperature, were added 7.5 mL of aq. HCl 30% w/w solution. The pH had to be around 6-8 (if not, the pH have to be corrected by addition of aqueous NaOH or HCl). Then 250 mL of H$_2$O was removed under vacuum at 50° C. Then the solution was heated to 80° C. and 41 mL of HCl 30% w/w solution was added dropwise. The pH had to be <2.7 (if not, the pH can be corrected with ac. HCl). The obtained mixture was slowly cooled to room temperature; an off white solid precipitated from the mixture. The suspension was stirred for 3 hours at room temperature, then the solid was isolated by filtration and dried at 40° C. for 8 hrs under vacuum. The product, 140 g (molar yield of 89.74%), was obtained as a white crystals, having chemical purity of 98.1% A/A % HPLC.

Example 3: Preparation of 2,4,5-Trifluorophenylacetic Acid, Compound (II)

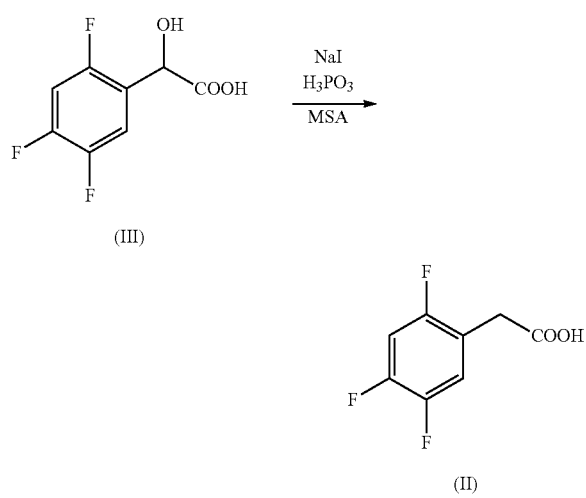

Material table

| Material | Amount | MW | Eq |
|---|---|---|---|
| Compound (III) | 10.0 g | 206.12 | 1 eq |
| H3PO3 | 23.9 g | 82 | 6 eq |
| Methanesulfonic acid | 20 mL | 96.11 | 2.0 V |
| NaI | 0.73 g | 149.89 | 1 eq |
| methyl tert-butyl ether | 30 mL | — | 3.0 V |
| toluene | 36 mL | — | 3.6 V |

A 100 mL flask was charged with 10.0 g of 2,4,5-trifluoromandelic acid (compound of formula (III)), 23.9 g of $H_3PO_3$ (6 eq.), 0.73 g of NaI (0.1 eq.) and 20 mL (2V) of methanesulfonic acid (abbreviated MSA).

The obtained mixture was stirred at 95-105° C. for 10 hours. Once the conversion is completed (by HPLC; conversion >99%) (at this stage, at the end of the reaction, the product TFPAA has chemical purity of 95.0% HPLC A/A %), the mixture is cooled to temperature below 30° C., then, and 20 mL of methyl tert-butyl ether were added and then, 20 mL of water were added. The obtained mixture was stirred for 5 min., then the organic layers were separated. Then 10 mL of methyl tert-butyl ether was added to the aqueous layers, stirred for 5 min, then the phase were separated.

The organic layer were combined.

The combined organic layers was concentrated under vacuum at 35° C., to provide the crude TFPAA (of formula (II)), 8.2 g, molar yield 88.4%, chemical purity HPLC A/A % 95.0%.

To the obtained crude TFPAA was recrystallized from toluene (36 mL), to obtain TFPAA as a white crystals, 7.4 g, molar yield 79.5%, chemical purity HPLC 99.77%, Impurities: compound (III) 0.12%, any other impurity <0.1%. Melting point: 121.5° C.

Example 4: Preparation of 2,4,5-Trifluorophenylacetic Acid, Compound (II)

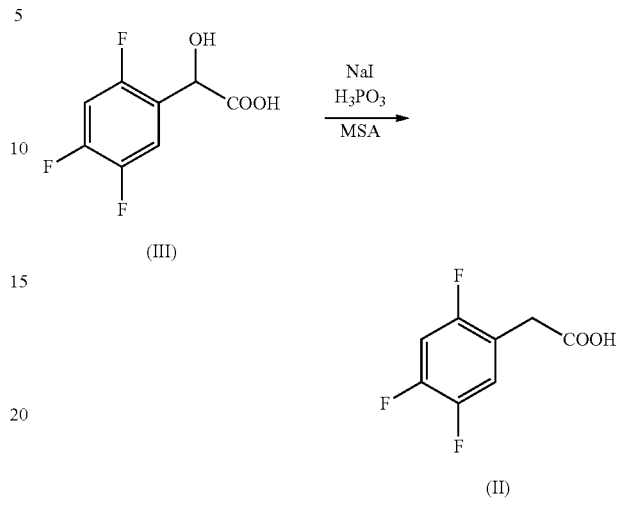

A 100 mL flask was charged 10.0 g of 2,4,5-trifluoromandelic acid compound (III), 23.9 g of $H_3PO_3$ (6 eq.), 0.73 g of NaI (0.1 eq.) and 0.47 g (0.10 eq.) of MSA. The obtained mixture was stirred at 95-105° C. for 24 hrs. Once the conversion is completed (by HPLC; conversion >99%, typically achieved after 24 hours), the mixture is cooled to room temperature, and 20 mL of methyl tert-butyl ether were added and then 20 mL of water where added. The obtained mixture was stirred for 5 min, then the organic layers were separated. Then 10 mL of methyl tert-butyl ether was added to the aqueous layers, stirred for 5 min, then the phase were separated. The organic layers were combined. The combined organic layers were concentrated under vacuum at 35° C., to provide crude TFPAA. To the obtained crude TFPAA was recrystallized from toluene, to obtain TFPAA, as a white crystals, 6.4 g, molar yield 69.5%, chemical purity of HPLC 99.47% A/A %.

Example 5: Preparation of 2,4,5-Trifluorophenylacetic Acid, Compound (II)

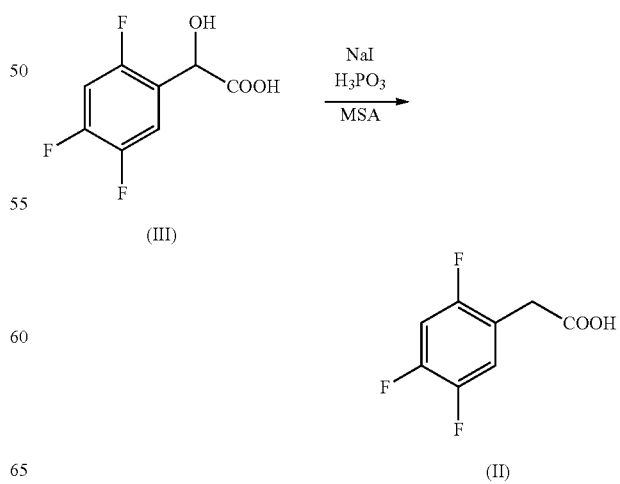

A 100 mL flask was charged 10.0 g of 2,4,5-trifluoromandelic acid compound (III), 15.7 g of H$_3$PO$_3$ (4 eq.), 0.73 g of NaI (0.1 eq.) and 0.47 g (0.10 eq.) of MSA. The obtained mixture was stirred at 95-105° C. for 18 hrs. Once the conversion is completed (by HPLC; conversion >99%, typically achieved after 18 hours), the mixture is cooled to room temperature, and 20 mL of methyl tert-butyl ether were added and then 20 mL of water where added. The obtained mixture was stirred for 5 min, then the organic layers were separated. Then 10 mL of methyl tert-butyl ether was added to the aqueous layers, stirred for 5 min, then the phase were separated. The organic layers were combined. The combined organic layers were concentrated under vacuum at 35° C., to provide crude TFPAA, as a white crystals, 8.5 g, molar yield 92%, chemical purity of HPLC 80.3% A/A %.

Example 6: Preparation of 2,4,5-Trifluorophenylacetic Acid, Compound (II)

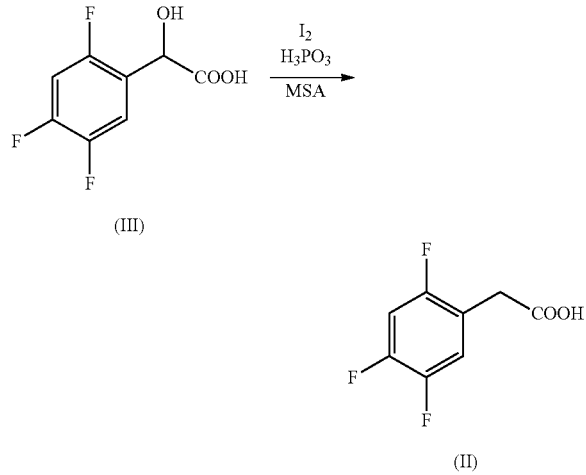

| Material table | | | |
|---|---|---|---|
| Material | Amount | MW | Eq |
| Compound (III) | 10.0 g | 206.12 | 1 eq |
| H3PO3 | 23.9 g | 82 | 6 eq |
| Methanesulfonic acid | 20 mL | 96.11 | 2.0 V |
| I$_2$ | 1.23 g | 253.8 | 0.1 eq |
| methyl tert-butyl ether | 30 mL | — | 3.0 V |
| toluene | 36 mL | — | 3.6 V |

A 100 mL flask was charged with 10.0 g of 2,4,5-trifluoromandelic acid (compound of formula (III)), 23.9 g of H$_3$PO$_3$ (6 eq.), 1.23 g of I$_2$ (0.1 eq.) and 20 mL (2V) of MSA). The obtained mixture was stirred at 95-105° C. for 18 hours. Once the conversion is completed (by HPLC; conversion >99%), the mixture is cooled to temperature below 30° C., then, and 20 mL of methyl tert-butyl ether were added and then, 20 mL of water were added. The obtained mixture was stirred for 5 min., then the organic layers were separated. Then 10 mL of methyl tert-butyl ether was added to the aqueous layers, stirred for 5 min, then the phase were separated. The organic layer were combined. The combined organic layers was concentrated under vacuum at 35° C., to provide the crude TFPAA. To the obtained crude TFPAA was recrystallized from toluene (36 mL), to obtain TFPAA as a white crystals, 7.0 g, molar yield 75%, chemical purity HPLC 99.6%.

Example 7: Preparation of 2,4,5-Trifluorophenylacetic Acid, Compound (II)

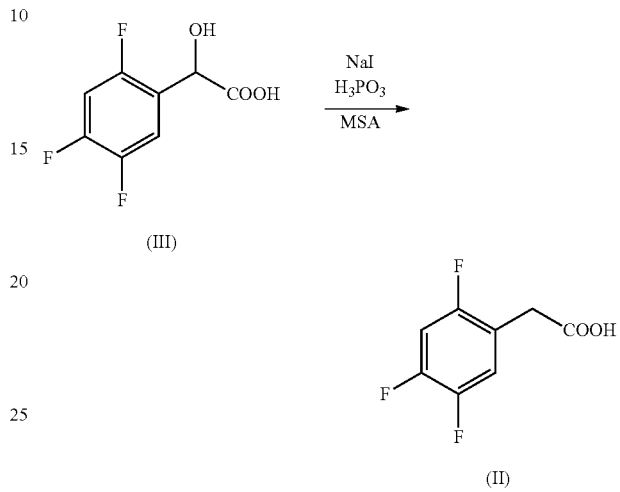

A 100 mL flask was charged 10.0 g of 2,4,5-trifluoromandelic acid compound (III), 15.3 g of H$_3$PO$_3$ (4 eq.), 1.23 g of I$_2$ (0.1 eq.) and 0.47 g (0.10 eq.) of MSA. The obtained mixture was stirred at 95-105° C. for 18 hrs. Once the conversion is completed (by HPLC; conversion >99%, typically achieved after 18 hours), the mixture is cooled to room temperature, and 20 mL of methyl tert-butyl ether were added and then 20 mL of water where added. The obtained mixture was stirred for 5 min, then the organic layers were separated. Then 10 mL of methyl tert-butyl ether was added to the aqueous layers, stirred for 5 min, then the phase were separated. The organic layers were combined. The combined organic layers were concentrated under vacuum at 35° C., to provide crude TFPAA. To the obtained crude TFPAA was recrystallized from toluene, to obtain TFPAA, as a white crystals, 7.26 g, molar yield 78%, chemical purity of HPLC 99.47% A/A %.

Example 8: Analytical Method to Analyse 2,4,5-Trifluorophenylacetic Acid.

Determination of purity, impurity profile and assay by HPLC:

Chromatographic Conditions:

Column: Water Symmetry C18, 250×4.6 mm, 5 μm particle diameter

Mobile phase A: 0.1% phosphoric acid (85%)

Mobile Phase B: acetonitrile

Gradient:

| Time (min) | % A | % B |
|---|---|---|
| 0 | 90 | 10 |
| 10 | 65 | 35 |

| Time (min) | % A | % B |
|---|---|---|
| 30 | 20 | 80 |
| 35 | 20 | 80 |

Detector: UV at 210 nm
Flow Rate: 1.0 mL/min.
Column Temperature: 20° C.
Injection volume: 2 μL for IPC; 10 μL (solid: 0.2 mg/ml)
Run time: 35 minutes
Equilibration time: 7 minutes
Diluent: Mobile phase A/Mobile phase B 50/50(v/v)

The present method has been used to determinate the chemical purity of both 2,4,5-Trifluoromandelic acid (compound (III)) and 2,4,5-Trifluorophenylacetic acid (compound (II)).

The invention claimed is:

1. A process for the preparation of Sitagliptin of formula (I) or salt thereof:

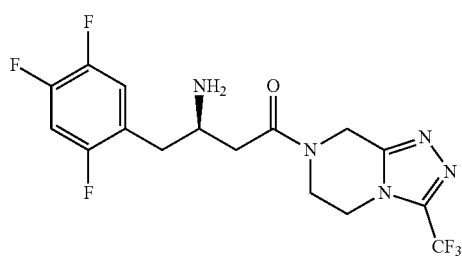

comprising:
A) preparing 2,4,5-trifluorophenylacetic acid of formula (II) or salt thereof:

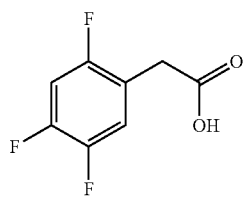

by directly converting the compound of (III):

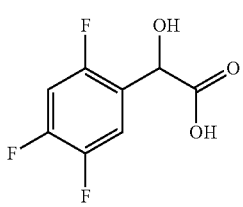

to the compound of formula (II) by reduction reaction; and
B) converting the 2,4,5-trifluorophenylacetic acid of formula (II) to Sitagliptin of formula (I) or salt thereof.

2. The process according to claim 1, wherein step B) is carried out by:

C) converting the 2,4,5-trifluorophenylacetic acid of formula (II) obtained in step A) to form the Ketoamide of formula (IV):

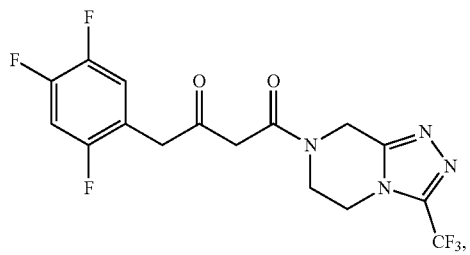

D) aminating the Ketoamide of formula (IV) produced in step C) to give the Enamine Amide of formula (V):

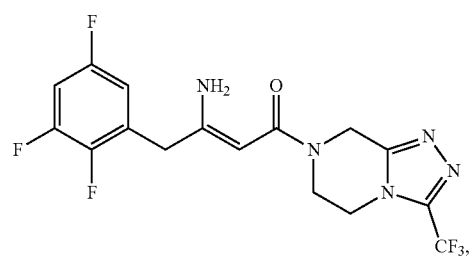

and
E) converting the Enamine Amide of formula (V) obtained in step D) to Sitagliptin of formula (I):

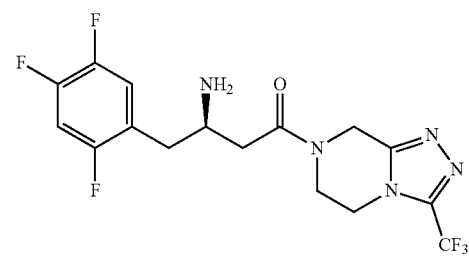

or by means of the alternative method for obtaining Sitagliptin of formula (I) consisting of the following steps:
D1) enzymatically converting the Ketoamide of formula (IV), obtained in the step C), to Sitagliptin of formula (I):

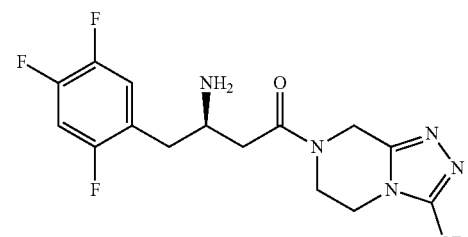

3. The process according to claim 1, wherein the compound of formula (III):

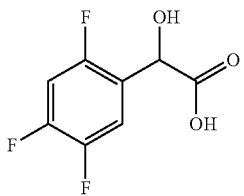

(III)

is prepared by:
a) acylating the 1,3,4-trifluorobenzene of formula (VI):

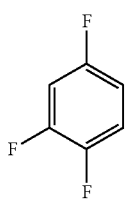

(VI)

with dichloroacetylchloride to give the compound of formula (VII):

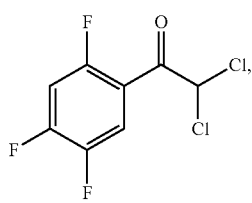

(VII)

and
b) converting the compound of formula (VII) to the compound of formula (III):

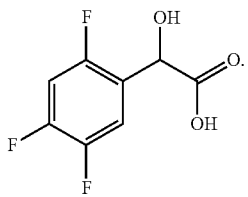

(III)

4. The process according to claim 1, wherein the reduction reaction of step A) is carried out in presence of iodide catalyst.

5. The process according to the claim 4, wherein the iodide catalyst is selected from the group consisting of iodine, sodium iodide, potassium iodide, hydroiodic acid, lithium iodide, and ammonium iodide.

6. The process according to claim 5, wherein the iodide catalyst is sodium iodide.

7. The process according to claim 5, wherein the iodide catalyst is iodine.

8. The process according to claim 1, wherein the reduction reaction of step A) is carried out in presence of a phosphorus and/or sulphurous reductant.

9. The process according to claim 8, wherein the phosphorus and/or sulphurous reductant is selected from the group consisting of phosphorous acid, hypophosphorous acid, pyrophosphoric acid, triphosphoric acid, trimetaphosphoric acid, hypophosphoric acid, red phosphorus, sulfurous acid, pyrosulfurous acid, peroxymonosulfuric acid, and hyposulfurous acid.

10. The process according to the claim 8, wherein the phosphorus and/or sulphurous reductant is phosphorous acid.

11. The process according to claim 1, wherein the reduction reaction of step A) is carried out in an acid solvent or an aqueous acid mixture thereof.

12. The process according to the claim 11, wherein the acid solvent or an aqueous acid mixture thereof is selected from the group consisting of hydrobromic acid, acetic acid, and methansulphonic acid.

13. The process according to claim 1, wherein the reduction reaction of step A) is carried out in presence of iodide catalyst and with a phosphorus and/or sulphurous reductant and is carried out in an acid solvent or an aqueous acid mixture thereof.

14. The process according to claim 13, wherein the acid solvent or an aqueous acid mixture thereof is selected from the group consisting of hydrobromic acid, acetic acid and methansulphonic acid.

15. The process according to claim 13, wherein the iodide catalyst is sodium iodide, the phosphorus and/or sulphurous reductant is phosphorous acid, and the acid solvent or an aqueous acid mixture thereof is selected from the group consisting of hydrobromic acid, acetic acid and methansulphonic acid.

16. The process according to claim 14, wherein the acid solvent or an aqueous acid mixture thereof is methanesulphonic acid.

17. A process for the preparation of 2,4,5-trifluorophenylacetic acid of formula (II) or salt thereof:

(II)

by comprising directly converting the compound of (III):

(III)

to the compound of formula (II),
wherein said direct conversion is carried out by reduction reaction.

18. The process according to claim 17, wherein the reduction reaction is carried out in the presence of iodide catalyst.

19. The process according to claim 17, wherein the reduction reaction is carried out in the presence of a phosphorus and/or sulphurous reduction.

20. The process according to claim 17, wherein the reduction reaction of step A) is carried out in an acid solvent or an aqueous acid mixture thereof.

\* \* \* \* \*